US010988453B2

(12) United States Patent
Andreux et al.

(10) Patent No.: US 10,988,453 B2
(45) Date of Patent: *Apr. 27, 2021

(54) COMPOSITIONS COMPRISING AN UROLITHIN COMPOUND

(71) Applicant: Amazentis SA, Ecublens (CH)

(72) Inventors: Penelope Andreux, Eclepens (CH); Christopher L. Rinsch, Morges (CH); William Blanco-Bose, Lausanne (CH)

(73) Assignee: Amazentis SA, Ecublens (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/589,890

(22) Filed: Oct. 1, 2019

(65) Prior Publication Data

US 2020/0140405 A1 May 7, 2020

Related U.S. Application Data

(63) Continuation of application No. 15/757,296, filed as application No. PCT/EP2016/070257 on Aug. 26, 2016, now Pat. No. 10,442,784.

(30) Foreign Application Priority Data

Aug. 28, 2015 (GB) ..................... 1515391

(51) Int. Cl.
| | |
|---|---|
| *C07D 311/80* | (2006.01) |
| *A61K 9/00* | (2006.01) |
| *A61K 9/14* | (2006.01) |
| *A23L 2/66* | (2006.01) |
| *A23L 33/19* | (2016.01) |
| *A61K 9/06* | (2006.01) |
| *A61K 38/01* | (2006.01) |
| *A61K 47/42* | (2017.01) |
| *A61K 9/08* | (2006.01) |
| *A61K 31/37* | (2006.01) |
| *A23L 2/52* | (2006.01) |
| *A61P 21/00* | (2006.01) |
| *A61P 25/00* | (2006.01) |
| *A23C 9/13* | (2006.01) |
| *A61K 31/366* | (2006.01) |
| *A61K 38/17* | (2006.01) |
| *A23L 33/00* | (2016.01) |
| *A23L 33/105* | (2016.01) |

(52) U.S. Cl.
CPC .......... *C07D 311/80* (2013.01); *A23C 9/1307* (2013.01); *A23L 2/52* (2013.01); *A23L 2/66* (2013.01); *A23L 33/19* (2016.08); *A61K 9/0056* (2013.01); *A61K 9/0095* (2013.01); *A61K 9/06* (2013.01); *A61K 9/08* (2013.01); *A61K 9/146* (2013.01); *A61K 31/366* (2013.01); *A61K 31/37* (2013.01); *A61K 38/01* (2013.01); *A61K 38/018* (2013.01); *A61K 38/1709* (2013.01); *A61K 47/42* (2013.01); *A61P 21/00* (2018.01); *A61P 25/00* (2018.01); *A23L 33/105* (2016.08); *A23L 33/40* (2016.08); *A23V 2002/00* (2013.01)

(58) Field of Classification Search
None
See application file for complete search history.

(56) References Cited

U.S. PATENT DOCUMENTS

| 10,442,784 B2 | 10/2019 | Andreux et al. |
| 2005/0282781 A1 | 12/2005 | Ghosal |
| 2020/0140405 A1 | 5/2020 | Andreux et al. |

FOREIGN PATENT DOCUMENTS

| AU | 2013/101214 A4 | 10/2013 |
| IN | 392/CHE/2004 | 2/2006 |
| WO | WO-2008/016554 A1 | 2/2008 |
| WO | WO-2012/088519 A2 | 6/2012 |
| WO | WO-2014/004902 A2 | 1/2014 |
| WO | WO-2014/111580 A1 | 7/2014 |
| WO | WO-2015/097231 A1 | 7/2015 |

OTHER PUBLICATIONS

International Search Report and Written Opinion for International Application No. PCT/EP2016/070257 dated Dec. 19, 2016.
Australian Examination Report for Application No. AU 2016314988 dated Feb. 21, 2020.
International Preliminary Report on Patentability for International Application No. PCT/EP2016/070257 dated Mar. 6, 2018.

*Primary Examiner* — Brian J Davis
(74) *Attorney, Agent, or Firm* — Dana M. Gordon; Foley Hoag LLP

(57) ABSTRACT

The invention provides compositions comprising a source of protein and a urolithin. The invention also provides uses and methods associated with, or making use of the compositions, such as a medicament, dietary supplement, functional food or medical food and in the treatment and/or prophylaxis of a muscle-related pathological condition. The invention also provides kits comprising urolithin and protein.

21 Claims, 1 Drawing Sheet

COMPOSITIONS COMPRISING AN UROLITHIN COMPOUND

RELATED APPLICATIONS

This application is a continuation of U.S. patent application Ser. No. 15/757,296, filed Mar. 2, 2018, which was the United States National Stage application of PCT/EP2016/070257, filed Aug. 26, 2016, which claims the benefit of priority to United Kingdom Patent application serial number 1515391.9, filed Aug. 28, 2015.

FIELD

The current invention relates to nutritional and medical formulations of urolithins and protein, in particular Urolithin A and protein.

BACKGROUND

Low muscle mass or poor muscle performance are characteristics of many diseases and conditions.

Muscle-related pathological conditions include myopathies, neuromuscular diseases, such as Duchenne muscular dystrophy, acute sarcopenia, for example muscle atrophy and/or cachexia, for example associated with burns, bed rest, limb immobilization, or major thoracic, abdominal, neck and/or orthopedic surgery. Age-related muscle-loss is an especially prevalent condition. Cachexia due to prolonged immobilization or other diseases, for example cancer, are other conditions that are often characterised by poor muscle performance.

Good muscle performance is important for effective living at all stages of life in healthy individuals as well as in those individuals suffering from a disease, especially the elderly. Improved muscle performance is of particular interest to athletes. For example an increase in muscular contraction strength, increase in amplitude of muscle contraction, or shortening of muscle reaction time between stimulation and contraction are all of benefit to individuals, especially athletes.

In severe cases of muscular atrophy, an anabolic steroid such as methandrostenolone is administered to patients to assist in the curative process. Such drugs can have numerous side-effects so their long-term use is preferably avoided.

Since the absence of muscle-building amino acids can contribute to muscle wasting, amino acid therapy is beneficial for regenerating damaged or atrophied muscle tissue, and for building muscle mass. The branched-chain amino acids or BCAAs (leucine, isoleucine, and valine) are important to this process, in addition to lysine and other amino acids.

Protein-containing nutritional products are available that are specifically formulated to increase muscle mass, improve muscle performance and/or reduce muscle wasting in elderly or hospitalised individuals. In general, it is necessary to exercise regularly for the desired improvements to be achieved.

SUMMARY OF THE INVENTION

The present invention provides a composition comprising:
a) a source of protein; and
b) a compound of formula (I) or a salt thereof:

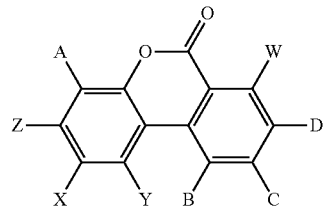

wherein:
A, B, C and D are each independently selected from H and OH;
W, X and Y are each independently selected from H and OH; and
Z is selected from H and OH.

Compounds of Formula (I) are members of the Urolithin family; in particular, the compound of Formula (I) is Urolithin A. Administration of a composition of protein and Urolithin A has been found to have a surprisingly beneficial and enhanced effect compared with administration of protein on its own. The composition of the invention is thus useful in the treatment diseases and conditions characterised by low muscle mass or poor muscle performance, and in the enhancement of muscle growth and/or muscle performance. It is also useful in maintaining muscle function.

In general, it is necessary for a subject to exercise in order for amino acid/protein treatments to have an optimal effect. There is evidence that the compositions of the invention are effective in enhancement of muscle function in the absence of exercise, or with less exercise being necessary.

The invention further provides a composition of the invention for use in the treatment of muscle-related pathological conditions. The invention also provides a method of treating a muscle-related pathological condition in a subject comprising administering to the subject an effective amount of a composition of the invention. The invention provides a composition of the invention for use in enhancing muscle performance. The invention also provides a method of enhancing muscle performance by administering to a subject an effective amount of a composition of the invention.

In a treatment of the invention, it is not essential for the Urolithin and protein to be administered simultaneously as part of a single composition. The invention also provides a method of treating a muscle-related pathological condition in a subject, or enhancing muscle function in a subject comprising administering to the subject an effective amount of a urolithin (for example Urolithin A) and an effective amount of protein. The urolithin and the protein can be administered at the same time or separated by a time interval. The invention further provides a kit comprising urolithin and protein for use in such a method. The amount of each of the urolithin and the protein that is administered is as described herein below for unit doses of compositions of the invention.

The invention further provides a compound of Formula (I) or a salt thereof having $D_{50}$ size in the range 0.5 to 50 µm and a $D_{90}$ size in the range 5 to 100 µm. Preferably, the compound or salt has a $D_{90}$ size in the range 8.2 to 16.0 µm, a $D_{50}$ size in the range 2.8 to 5.5 µm and a $D_{10}$ size in the range 0.5 to 1.0 µm. It has been found that the compounds of the invention with those particle sizes have good dispersion and dissolution properties, and enhanced bioavailability.

DETAILED DESCRIPTION

Figure 1:
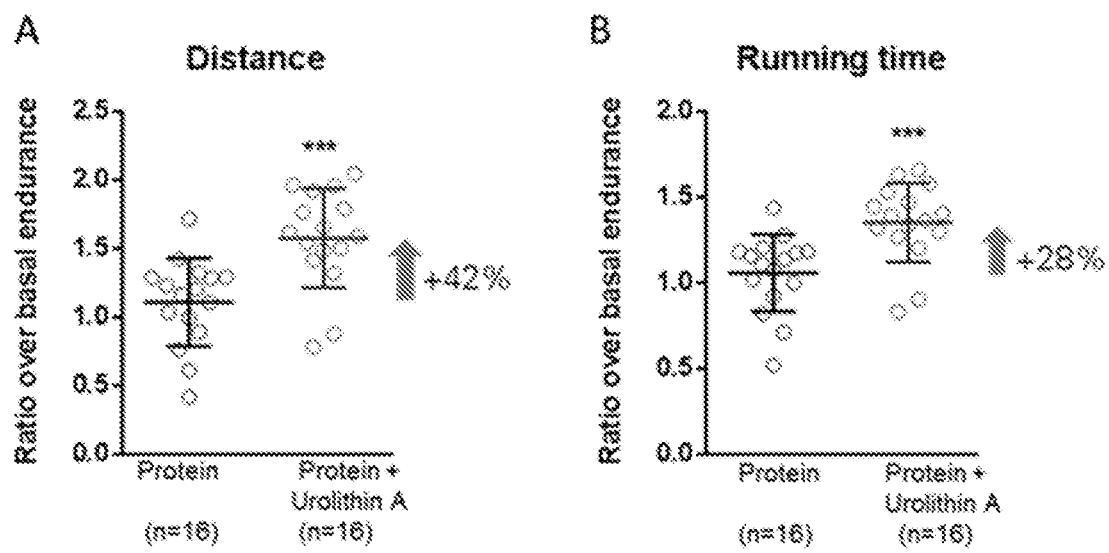
FIG. 1 shows the results of a muscle endurance experiment in which mice were fed with either a high protein diet alone or a high protein diet containing Urolithin A.
Figure 2:
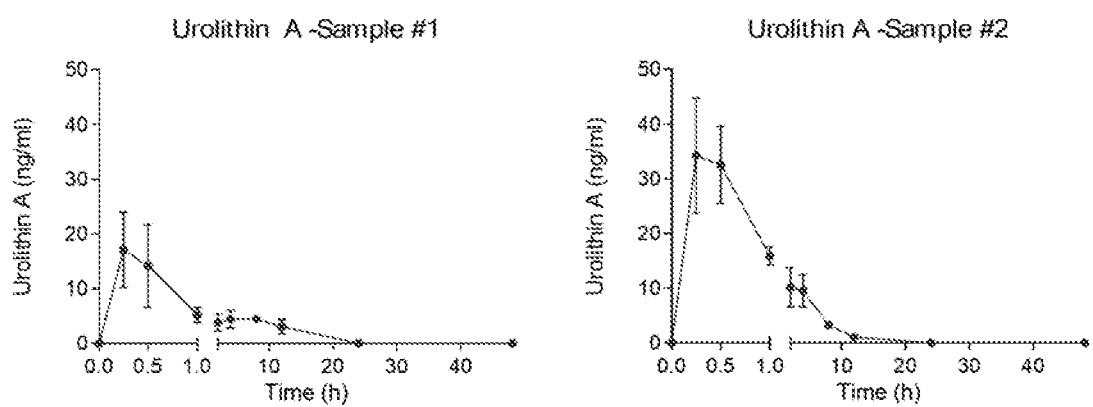
FIG. 2 shows the results of experiments in which rats were fed with formulations comprising Urolithin A at a variety of different particle sizes and the level of the Urolithin A in the blood was assessed.

As described above, the invention provides a composition comprising a source of protein and a urolithin.

The protein in the composition of the invention is preferably purified protein; that is to say that it has been isolated from the native food ingredient that it was created in. The protein content, as assessed by weight %, in a composition of the invention is preferably higher than in most unprocessed food ingredients. The protein typically makes up at least 15% w/w of the composition of the invention. The protein preferably makes up 20% w/w or more of the composition, for example 25% w/w or more by weight, for example 30% w/w or more by weight, for example 40% w/w or more of the composition, for example 50% w/w or more of the composition, for example 55% w/w or more of the composition, for example 60% w/w or more of the composition. For example the protein may make up 20-99% w/w of the composition, for example 20-90% w/w of the composition, for example, 30-80%/w of the composition, for example 40-80%/w of the composition, for example 50-80%/w of the composition, for example 40-70%/w of the composition.

The weight ratio between the protein component and the urolithin is generally in the range 3:1 to 5000:1, for example 3:1 to 1000:1, for example 5:1 to 1000:1; for example 3:1 to 500:1, for example 3:1 to 250:1, for example 5:1 to 500:1; for example 5:1 to 200:1; for example 5:1 to 100:1; for example 5:1 to 50:1; for example 5:1 to 20:1, for example 6:1 to 15:1. Alternatively, the ratio can be for example in the range of 10:1 to 500:1, for example in the range 10:1 to 100:1, for example 20:1 to 50:1, for example 30:1 to 40:1. In some embodiments, the ratio can be in the range 50:1 to 5000:1; for example 70:1 to 2000:1, for example 100:1 to 500:1. The composition of the invention can be provided as a single serving supplement to a subject's general diet (for example as a bar or a drink); alternatively, it can be provided as a part or the whole of every meal. The weight ratio between the protein component and the urolithin is generally higher if the composition is provided as a part or the whole of every meal than if it is provided as a single serving supplement to a subject's general diet.

The urolithin typically makes up from 0.05 to 10% w/w of the composition of the invention, for example 0.1 to 10% w/w. For example the urolithin may make up 0.2-8% w/w of the composition, for example 0.2-5% w/w of the composition, for example, 0.3-3%/w of the composition, for example 0.5-2% w/w of the composition. In some embodiments, the urolithin may make up 0.05-5% w/w of the composition, for example 0.1-2% w/w of the composition, for example, 0.2-1%/w of the composition. In some embodiments, the urolithin may make up from 0.05 to 80% w/w of the composition, for example from 0.1 to 75% w/w of the composition.

Sources of Protein:

Non-limiting examples of suitable protein or sources thereof for use in the compositions include hydrolyzed, partially hydrolyzed or non-hydrolyzed proteins or protein sources. They may be derived from any known or otherwise suitable source such as milk (e.g., casein, whey), animal (e.g., meat, fish), cereal (e.g., rice, corn) or vegetable (e.g., soy, pea) sources. Combinations of sources or types of proteins may be used. Non-limiting examples of proteins or sources thereof include intact pea protein, intact pea protein isolates, intact pea protein concentrates, milk protein isolates, milk protein concentrates, casein protein isolates, casein protein concentrates, whey protein concentrates, whey protein isolates, sodium or calcium caseinates, whole cow's milk, partially or completely defatted milk, yoghurt, soy protein isolates and soy protein concentrates, and combinations thereof. Combinations of sources or types of proteins may be used.

Preferred proteins include pea protein, whey protein, soy protein and casein. Casein proteins may, for example, be or include sodium caseinate and calcium caseinate.

Mixtures of sources of proteins may have particular benefits. For example, two or more of pea protein, whey protein, soy protein and casein may be present. For example sodium caseinate, milk protein concentrate, and soy protein isolate may all be present. Combinations of casein protein and whey protein are especially preferred, for example containing 60 to 90% w/w whey protein and 10 to 40% w/w casein protein, for example 65 to 80% w/w whey protein and 20 to 35% w/w casein protein, for example 70% w/w whey protein and 30% w/w casein protein.

The source of protein may be provided by individual amino acids or polypeptide made up of many amino acids, or mixtures of those.

For many muscle growth, muscle maintenance and/or muscle enhancement treatments, it is beneficial for certain particular amino acids to be provided. For example, L-arginine, L-glutamine, lysine and the branched-chain amino acids (ie leucine, isoleucine, and valine; in particular leucine and isoleucine) are considered important. In certain embodiments, the source of protein contains a high proportion of those amino acids.

These particular amino acids may be provided as the source of protein, or they may be additional to a main source of protein. Thus, the source of protein in the composition of the invention may include one or more branched-chain amino acids (leucine, isoleucine, and valine). The source of protein in the composition of the invention may include one or both of L-arginine and L-glutamine. The source of protein in the composition of the invention may include lysine.

In a preferred composition, the protein component comprises whey protein and/or casein protein together with one or more individual amino acids, for example one or more of (or all of) leucine, isoleucine and L-arginine.

Urolithins:

Urolithins are metabolites produced by the action of mammalian, including human, gut microbiota on ellagitannins and ellagic acid. Ellagitannins and ellagic acid are compounds commonly found in foods such as pomegranates, nuts and berries. Ellagitannins are minimally absorbed in the gut themselves. Urolithins are a class of compounds with the representative structure (I) shown above. The structures of some particularly common urolithins are described in Table 1 below, with reference to structure (I).

|  | Substituent of structure (I) | | | | | |
| --- | --- | --- | --- | --- | --- | --- |
|  | A | B | C | D | W, X and Y | Z |
| Urolithin A | H | H | H | OH | H | OH |
| Urolithin B | H | H | H | H | H | OH |
| Urolithin C | H | H | OH | OH | H | OH |
| Urolithin D | OH | H | OH | OH | H | OH |
| Urolithin E | OH | OH | H | OH | H | OH |
| Isourolithin A | H | H | OH | H | H | OH |
| Isourolithin B | H | H | OH | H | H | H |
| Urolithin M-5 | OH | OH | OH | OH | H | OH |
| Urolithin M-6 | H | OH | OH | OH | H | OH |
| Urolithin M-7 | H | OH | H | OH | H | OH |

In practice, for commercial scale products, it is convenient to synthesise the urolithins. Routes of synthesis are described, for example, in WO2014/004902.

Particularly suitable compounds for use in compositions of the invention are the naturally-occurring urolithins. Thus, Z is preferably OH and W, X and Y are preferably all H. When W, X and Y are all H, and A, and B are both H, and C, D and Z are all OH, then the compound is Urolithin C. When W, X and Y are all H, and A, B and C are all H, and D and Z are both OH, then the compound is Urolithin A. Preferably, the Urolithin used in a formulation of the invention is Urolithin A or Urolithin C. Most preferably, the Urolithin used in a formulation of the invention is Urolithin A.

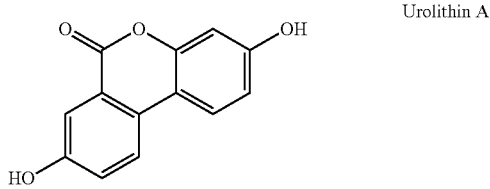 [SMILES: O=c1oc2cc(O)ccc2c2ccc(O)cc12]

Urolithin A

Preferably, urolithin for use in compositions of the invention is micronized. It has been found by the current inventors that micronized urolithin can be dissolved or suspended more rapidly and more effectively than unmicronised urolithin.

The invention further provides micronized urolithin. The invention further provides a composition contained micronized urolithin. Micronized urolithin preferably has a $D_{50}$ size of under 100 µm—that is to say that 50% of the urolithin by mass has a particle diameter size of under 100 µm. More preferably, the urolithin has a $D_{50}$ size of under 75 µm, for example under 50 µm, for example under 25 µm, for example under 20 µm, for example under 10 µm. More preferably, the urolithin has a $D_{50}$ in the range 0.5-50 µm, for example 0.5 to 20 µm, for example 0.5 to 10 µm, for example 1 to 10 µm, for example 2.8 to 5.5 µm. Preferably, the urolithin has a $D_{90}$ size of under 100 µm—that is to say that 90% of the urolithin by mass has a particle diameter size of under 100 µm. More preferably, the urolithin has a $D_{90}$ size of under 75 µm, for example under 50 µm, for example under 25 µm, for example under 20 µm, for example under 15 µm. The urolithin preferably has a $D_{90}$ in the range 5 to 100 µm, for example 5 to 50 µm, for example 5 to 20 µm, for example 8.2 to 16.0 µm. Preferably, the urolithin has a Dm in the range 0.5-1.0 µm. Preferably, the urolithin has a $D_{90}$ in the range 8.2 to 16.0 µm, a $D_{50}$ in the range 2.8 to 5.5 µm and a $D_{10}$ in the range 0.5 to 1.0 µm. Micronisation can be achieved by methods established in the art, for example compressive force milling, hammermilling, universal or pin milling, or jet milling (for example spiral jet milling or fluidised-bed jet milling) may be used. Jet milling is especially suitable.

Forms of Compositions:

The compositions of the invention can take any suitable physical form. They may be in the form of a solid (for example a tablet or a bar), a semi-solid (for example a softgel, capsule (for example a hard capsule) or dragee), a powder or a liquid (including emulsions). The compositions of the invention may be pharmaceutical compositions. The compositions of the invention may be nutritional compositions.

Tablet form compositions may be of any suitable type, and they may contain excipients conventional in the art. The excipients can, for example, provide a desired hardness, shelf-life and flavour such that the composition has an acceptable taste, an attractive appearance and good storage stability. A bar may be of any suitable type and it may contain ingredients conventionally used for the preparation of snack bars.

Semi-solid forms may likewise contain excipients conventional in the art. The excipients can, for example, provide a desired hardness, shelf-life and flavour such that the composition has an acceptable taste, an attractive appearance and good storage stability.

Powders are commonly used for the supply of nutritional and medical compositions. Powders have the advantage that multiple doses can be provided in a simple container, and doses of various sizes can be used from the same supplied container. Powders generally have good storage properties. Powder compositions may also contain excipients conventional in the art. The excipients can, for example, provide a shelf-life, flavour and moisture resistance such that the composition has an acceptable taste, an attractive appearance and good storage stability. Protein powders are widely available on the market. The current invention may take the form of a kit comprising a protein powder composition together with a separate solid or liquid composition containing urolithin. A solid or liquid composition containing urolithin (for example a tablet or a drink, or other form described herein) may be provided with instructions for use together with a protein powder. The current invention may take the form of a protein powder mixed with urolithin.

Liquid compositions may be in the form of a medicine, in the form of a drink. Liquid formulations may be solutions, emulsions, slurries or other semi-liquids. Excipients in a liquid composition can, for example, provide a shelf-life, visual appearance, flavour and mouthfeel such that the composition has an acceptable taste, an attractive appearance and good storage stability.

Compositions may be in the form of a yoghurt. For example, Greek- and Icelandic-style yoghurts are known to commonly have an especially high protein content which makes them especially suitable for use in formulations of the invention. Yoghurts for use in compositions of the invention may contain, for example, from 2 to 15 g of protein per 100 g. Particularly preferred are yoghurts with a high protein content, for example from 6 to 15 g per 100 g, for example from 7 to 15 g per 100 g, for example from 8 to 15 g per 100 g. The yogurts for use in compositions of the invention may be either spoonable or drinkable in format. Optionally, supplemental protein may also be added to a yoghurt formulation to increase the protein content of the formulation. Yoghurts of the invention may contain live cultures, such as S. thermophilus, L. bulgaricus. and/or L. acidophilus. L. lactis.

Additional Components in Compositions of the Invention:

The composition according to the invention may contain additional components beyond the urolithin and the protein. The additional components may be compounds that provide health benefits, for example selected from vitamins, minerals, polyunsaturated fatty acids, functional amino acids and other compounds.

Amongst vitamins, there may specifically be mentioned Vitamin A, Vitamin C, Vitamin D, Vitamin B12 and Vitamin K2. As used herein, "vitamin D" refers, to any of known form of vitamin D, and specifically includes vitamin $D_2$ (ergocalciferol), vitamin $D_3$ (cholecalciferol), vitamin D precursors, metabolites and another analogues, and combinations thereof, as well as the various active and inactive forms of vitamin D. For example, vitamin $D_3$ may be provided in its unhydroxylated inactive form as cholecalciferol, or may be provided in its hydroxylated active form as calcitriol.

Creatine has been described as having beneficial effects in the treatment of muscle disorders. It can be included in compositions of the invention. β-hydroxyl-β-methylbutyrate (HMB) has been described as having beneficial effects in the treatment of muscle disorders. It can be included in compositions of the invention.

Amongst minerals, there may specifically be mentioned calcium salts (for example calcium phosphate), selenium, and iron salts.

Polyunsaturated fatty acids are fatty acids that contain more than one double bond in the backbone. This class includes many important compounds, such as essential fatty acids, e.g., omega-3 and omega-6 fatty acids. Long chain polyunsaturated fatty acids are suitable, and preferably those having at least 20 carbon atoms in the molecule. Such long chain omega-3 fatty acids include cis-11, 14, 17-eicosatrienoic acid (ETE) C20:3, cis-8, 11, 14, 17-eicosatetraenoic acid (ETA) C20:4, cis-5,8, 11, 14, 17-eicosapentaenoic acid (EPA) C20:5, cis-7, 10, 13, 16, 19-docosapentaenoic acid (DPA, Clupanodonic acid) C22:5, cis-4, 7, 10, 13, 16, 19-docosahexaenoic acid (DHA) C22:6, cis-9, 12, 15, 18,21-tetracosapentaenoic acid C24:5; cis-6,9, 12, 15, 18,21-tetracosahexaenoic acid (Nisinic acid) C24:6. Long chain omega-6 fatty acids having at least 20 carbon atoms include cis-11, 14-eicosadienoic acid C20:2, cis-8, 11, 14-eicosatrienoic acid (Dihomo-gamma-linolenic acid) (DGLA) C20:3, cis-5,8, 11, 14-eicosatetraenoic acid (Arachidonic acid) (AA) C20:4, cis-13, 16-docosadienoic acid C22:2, cis-7, 10, 13, 16-docosatetraenoic acid (Adrenic acid) C22: 4, cis-4, 7, 10, 13, 16-docosapentaenoic acid (Osbond acid) C22:5. The composition according to the invention preferably contains EPA, DHA or a combination of them, for example in an amount from 10 to 1,000 mg; for example in an amount from 25 to 250 mg.

For many muscle growth and/or muscle enhancement treatments, it is beneficial for certain particular amino acids to be provided. For example, L-arginine, L-glutamine, lysine and the branched-chain amino acids are considered important. These amino acids are sometimes known as "functional amino acids". The composition of the invention may include one or more branched-chain amino acids (leucine, isoleucine, and valine). The composition of the invention may include one or both of L-arginine and L-glutamine. The composition of the invention may include lysine.

Pharmaceutical compositions of the invention may include additional pharmaceutically active compounds.

A composition of the invention may include one or more agents that are useful for mitochondrial biogenesis or the treatment of mitochondrial disorders. Such compounds include, without limitation, resveratrol, pyrroloquinoline quinone, genistein, hydroxyltyrosol, quercetin, L-carnitine, alpha-lipoic acid, and folinic acid (e.g., as leucovorin).

Additional compounds may further (or alternatively) be included in a composition of the invention, including for example tomatidine, ursolic acid, curcumin, capsaicin, menthol, trolamine salicylate and methylsalicylate.

In some exemplary embodiments, the compositions of the present disclosure may comprise, in addition to protein and urolithin, one or more additional macronutrients, typically fat or carbohydrate, or both fat and carbohydrate.

Any suitable source of fat or oil of the type commonly used in the preparation of foodstuffs and pharmaceuticals may be used in compositions of the invention. Non-limiting examples of suitable sources of fats for use in the compositions described herein also include polyunsaturated fatty acids such as docosahexaenoic acid (DHA), arachidonic acid (ARA), eicosapentaenoic acid (EPA) and combinations thereof.

Non-limiting examples of suitable carbohydrates or sources thereof for use in the compositions described herein may include maltodextrin, hydrolyzed or modified starch or cornstarch, glucose polymers, corn syrup, corn syrup solids, rice-derived carbohydrates, glucose, fructose, lactose, high fructose corn syrup, tapioca dextrin, isomaltulose, sucromalt, maltitol powder, glycerin, fructooligosaccharides, soy fiber, corn fiber, guar gum, konjac flour, polydextrose, honey, sugar alcohols (e.g., maltitol, erythritol, sorbitol), and combinations thereof. Maltodextrin, sucrose and fructose are especially preferred.

The total concentrations or amounts of the protein, fat, carbohydrates and other components vary depending upon the nutritional needs of the intended user.

Additional components in a composition of the invention may be compounds that do not provide helath benefits to the subject, but instead improve the composition in some other way, for example its taste, texture or shelflife as mentioned above. The composition of the invention may thus further contain one or more compounds selected from emulsifiers, colorants, preservatives, gums, setting agents, thickeners, sweeteners and flavourings.

Suitable emulsifiers, colorants, preservatives, gums, setting agents and thickeners are well known in the art of manufacture of emulsions and other semi-liquids. For example preservatives, such as benzoic acid, sorbic acid, phosphoric acid, lactic acid, acetic acid, hydrochloric acid and the soluble salts thereof may be used.

A sweetener may be especially beneficial in a composition of the invention. High potency non-nutritive carbohydrate sweetening agents may be used, for example selected from aspartame, sucrose, potassium acelsufame, saccharin, cyclamates, *Stevia*, thaumatin and mixtures thereof. Aspartame is especially suitable.

A flavouring may be especially beneficial in a composition of the invention. In a liquid or semi-liquid composition, fruit flavour can be provided by inclusion of a fruit sauce or puree. Typical flavorings include strawberry, raspberry, blueberry, apricot, pomegranate, peach, pineapple, lemon, orange and apple. Generally, fruit flavorings include fruit extract, fruit preserve or fruit puree, with any of a combination of sweeteners, starch, stabilizer, natural and/or artificial flavors, colorings, preservatives, water and citric acid or other suitable acid to control the pH.

Dosing

The effective amount of the composition to be taken will vary depending upon the manner of administration, the age, body weight, and general health of the subject. Factors such as the disease state, age, and weight of the subject may be important, and dosage regimens may be adjusted to provide the optimum response.

Conventional protein compositions are generally taken at a level of 5 to 30 g per serving, and a subject generally takes one, two or three servings per day. The daily dose of protein from the composition is thus generally in the range of 5 to 90 g, for example 5 to 80 g, for example 5 to 70 g, for example 5 to 60 g, for example 5 to 50 g, for example 10 to 40 g, for example 20 to 40 g.

For an elderly subject, recommended protein intake and exercise for optimal muscle function have been described, for example in: 'Recommendations from the ESPEN Expert Group': *Clinical Nutrition,* 33 (2014) 929e936. It is recommended: (a) for healthy older people, the diet should provide at least 1.0-1.2 g protein/kg body weight/day; (b) for older people who are malnourished or at risk of malnutrition because they have acute or chronic illness, the diet should provide 1.2-1.5 g protein/kg body weight/day, with even higher intake for individuals with severe illness or injury.

A unit dose composition of the invention preferably contains 5 to 90 g, for example 5 to 80 g, for example 5 to 70 g, for example 5 to 60 g of protein, for example 5 to 40 g of protein, for example 10 to 40 g of protein for example 10 to 30 g of protein. A unit dose may be in the form of a snack bar; a snack bar of weight 25 to 150 g, for example 40 to 100 g may contain the necessary amount of protein (such as 10 to 40 g of protein, or another amount mentioned above). A unit dose composition may alternatively be in the form of a drink, for example provided in a container (for example a pouch or a bottle) of a volume suitable for a single dose (for example 50 to 500 ml, for example 100 to 300 ml). A drink of 100 to 300 ml may contain the necessary amount of protein. A unit dose composition may alternatively be in the form of a powder to be reconstituted into a drink, for example a suitable quantity of powder for a single dose (for example 20 gr to 60 gr of powder, containing 10 gr to 40 gr of protein). A reconstituted drink of 100 to 500 ml may contain the necessary amount of protein.

Daily intake of the urolithin (for example Urolithin A) component is typically in the range of 10 mg to 5 g per day, for example 20 mg to 2500 mg per day, for example 20 mg to 500 mg per day, for example, 10 mg to 100 mg per day, for example 50 mg to 1500 mg per day, for example 250 mg to 1500 mg per day, for example 50 mg to 1000 mg per day, for example 20 mg to 250 mg per day, for example 250 mg to 1000 mg per day, for example 500 mg to 1000 mg per day, for example 750 mg to 1000 mg per day. In one embodiment, the composition is taken in an amount to provide a dosage of urolithin in the range from about 0.2 mg/kg/day to greater than about 100 mg/kg/day. For example, the dosage of urolithin may be 0.2 to 100, 0.2 to 50, 0.2 to 25, 0.2 to 10, 0.2 to 7.5, 0.2 to 5, 0.25 to 100, 0.25 to 25, 0.25 to 25, 0.25 to 10, 0.25 to 7.5, 0.25 to 5, 0.5 to 50, 0.5 to 25, 0.5 to 20, 0.5 to 15, 0.5 to 10, 0.5 to 7.5, 0.5 to 5, 0.75 to 50, 0.75 to 25, 0.75 to 20, 0.75 to 15, 0.75 to 10, 0.75 to 7.5, 0.75 to 5, 1.0 to 50, 1 to 25, 1 to 20, 1 to 15, 1 to 10, 1 to 7.5, 1 to 5, 2 to 50, 2 to 25, 2 to 20, 2 to 15, 2 to 10, 2 to 7.5, or 2 to 5 mg/kg/day.

A unit dose composition of the invention preferably contains 10 mg to 5 g of urolithin, for example 20 mg to 2500 mg, for example 50 mg to 1500 mg, for example 250 mg to 1500 mg, for example 50 mg to 1000 mg, for example 50 mg to 250 mg, for example 250 mg to 1000 mg. A unit dose may be in the form of a snack bar; a snack bar of weight 25 to 150 g (for example 40 to 100 g) may contain the necessary amount of urolithin. A unit dose composition may alternatively be in the form of a drink, for example provided in a container (for example a pouch) of a volume suitable for a single dose (for example 100 to 300 ml). A drink of 50 to 500 ml (for example 100 to 300 ml) may contain the necessary amount of urolithin. A drink providing the composition of the invention may contain the urolithin at a concentration of 0.1 to 50 mg per ml, for example 0.5 to 10 mg per ml, for example 1 to 5 mg per ml.

The weight ratio between the protein component and the urolithin is generally in the range 1:10 to 5000:1; for example 1:10 to 1:1; for example 1:2.5 to 5000:1; for example 1:2.5 to 1200:1; for example 1:1 to 1200:1; for example 1:1 to 600:1; for example 2:1 to 5000:1; for example 2:1 to 12000:1; for example 3:1 to 5000:1; for example 3:1 to 1200:1; for example 3:1 to 1000:1; for example 3:1 to 500:1; for example 3:1 to 250:1; for example 5:1 to 1200:1; for example 5:1 to 600:1; for example 5:1 to 500:1; for example 5:1 to 400:1; for example 5:1 to 200:1; for example 5:1 to 100:1; for example 5:1 to 80:1; for example 5:1 to 50:1; for example 5:1 to 20:1, for example 6:1 to 15:1. Alternatively, the ratio can be for example 10:1 to 500:1, for example 10:1 to 100:1, for example 20:1 to 50:1, for example 30:1 to 40:1. In some embodiments, the ratio can be in the range 50:1 to 5000:1; for example 70:1 to 2000:1, for example 100:1 to 500:1.

The urolithin typically makes up from 0.05 to 10% w/w of the composition of the invention, 0.1 to 10% w/w of the composition of the invention. For example the urolithin may make up 0.2-8% w/w of the composition, for example 0.2-5% w/w of the composition, for example, 0.3-3%/w of the composition, for example 0.5-2%/w of the composition. In some embodiments, the urolithin may make up 0.05-5% w/w of the composition, for example 0.1-2% w/w of the composition, for example, 0.2-1%/w of the composition.

A composition of the invention may thus contain 5 to 80 g of protein and 10 mg to 5 g of urolithin; for example 5 to 60 g of protein and 10 mg to 5 g of urolithin; for example 5 to 40 g of protein and 20 mg to 2500 mg; for example 5 to 40 g of protein and 50 mg to 1000 mg of urolithin; for example 10 to 30 g of protein and 50 mg to 1000 mg of urolithin; for example 10 to 30 g of protein and 50 mg to 500 mg of urolithin; for example 10 to 30 g of protein and 100 mg to 500 mg of urolithin. The compositions preferably further contain carbohydrates, vitamins and minerals. Representative compositions are shown in Tables 1, 2 and 3:

TABLE 1

Representative powder composition:

| Composition | Per 100 g |
| --- | --- |
| Protein | 10-80 g |
| Carbohydrates | 20-40 g |
| Fat | 0-20 g |
| Polyunsaturated Fatty Acids | 0-5 g |
| Fiber | 0-5 g |
| Vitamins | 0-100% of respective RDAs |
| Minerals | 0-100% of respective RDAs |
| Folic Acid | 0-1000 ug |
| Niacin | 0-100 mg |
| Creatine | 0-20 g |
| Urolithin A | 0.025-5 g |

In a bulk powder, the protein preferably makes up 20% or more of the powder by weight, for example 20% or more by weight, for example 30% or more by weigh, for example 40% or more by weight of the powder. For example the protein may make up 20-90% by weight of the powder, for example 30-80% by weight of the powder, for example 40-80% by weight of the powder, for example 40-70%, for example 60-80% by weight, for example 60-70% by weight of the powder.

Bulk powder is generally provided with instructions informing the subject how much of the powder to use for one serving. For example the bulk powder may be supplied in a container accompanied by a scoop of the necessary size to enable the correct amount of powder to be measured out. Powder may be taken neat, mixed with food, or added to water to make a drink.

TABLE 2

Representative drink composition:

| Composition | Per 100 mL |
|---|---|
| Protein (for example 100% Hydrolyzed Whey) | 5-15 g |
| Carbohydrates | 1-20 g |
| Fat | 0-9.5 g |
| Polyunsaturated Fatty Acids | 0-2.5 g |
| Fiber | 0-2 g |
| Vitamins | 0-100% of respective RDAs |
| Minerals | 0-100% of respective RDAs |
| Folic Acid | 0-500 ug |
| Niacin | 0-20 mg |
| Urolithin A | 10-2000 mg |

TABLE 3

Representative bar composition:

| Composition | Per bar of 35 g |
|---|---|
| Protein | 6.7 g |
| Carbohydrates | 10-20 g |
| Fat | 0-15 g |
| Polyunsaturated Fatty Acids | 2-6 g |
| Fiber | 0-5 g |
| Niacin | 0-100 mg |
| Vitamins | 0-100% of respective RDAs |
| Minerals | 0-100% of respective RDAs |
| L-Carnitine | 0-500 mg |
| Urolithin A | 10-2000 mg |

TABLE 4

Representative yoghurt composition:

| Composition | Per 100 g Yoghurt |
|---|---|
| Protein | 2-15 g |
| Carbohydrates | 3-20 g |
| Fat | 0-12 g |
| Calcium | 5-20% RDA |
| Fiber | 0-4 g |
| Vitamins | 0-100% of respective RDAs |
| Minerals | 0-100% of respective RDAs |
| Live Cultures | S. thermophilus, L. bulgaricus. L. acidophilus. L. lactis |
| Urolithin A | 10-2000 mg |

The composition of the invention can be taken as a single treatment or, more commonly, as a series of treatments. In one example, a subject takes a dose before or after exercise. For a subject who is not able to exercise, a dose of the composition may, for example, be taken once, twice or three times per day, or one, two, three, four, five or six times per week. It will also be appreciated that the effective dosage of the compound may increase or decrease over the course of a particular treatment.

Treatments:

The compositions of the invention find use in improving muscle performance, improving muscle function, preventing a decline in muscle function, increasing muscle mass and/or reducing muscle wasting. The improvement in muscle performance, improving or maintaining muscle function, the increase in muscle mass and/or reduction in muscle wasting may be as part of a medical treatment, or it may be for personal preference ("lifestyle") or cosmetic reasons. The compositions of the invention can be for use as a medicament. The compositions can be used as a dietary supplement, as a functional food, functional beverage, or as a medical food.

Most muscle enhancement regimes require the subject to exercise as well as taking a muscle enhancement composition. There is evidence that the combination of protein and urolithin of the invention is effective in enhancing muscle growth, muscle strength, muscle endurance and muscle function in the absence of exercise, or with less exercise being necessary.

The compositions find use in the treatment of both diseases and disease states. The compositions find use in the management normal physiological function in healthy individuals of conditions characterised by poor physical performance, impaired endurance capacity, and impaired muscle function. Compositions of the invention may improve physical performance in individuals with a disease, including young and elderly individuals. Compositions of the invention may improve physical performance, for example, short-term performance or long-term performance in healthy individuals, including athletes, non-athletic individuals, sedentary individuals and the elderly. This improvement of performance may be measured by the time spent to walk or run a certain distance (for example, an improved performance during the 6 minute walk test (MWT)), an improved time to run a certain distance, an improved IPAQ score on the international physical activity questionnaire, an increased number of chair-stands in a certain time, or another test designed to measure physical performance.

Compositions of the invention further provide for the improvement of endurance capacity. The endurance capacity refers to the time to fatigue when exercising at a constant workload, generally at an intensity <80% $VO_2$max. Compositions of the invention may improve endurance capacity in individuals with a disease, including young and elderly individuals. Compositions of the invention may improve endurance capacity in healthy individuals, including athletes, non-athletic individuals, sedentary individuals and the elderly. The invention provides for a method of increasing the time to fatigue while performing a specific activity, for example, fitness training, walking, running, swimming, or cycling. This improvement of endurance capacity may be assessed with objective measurements (for example, speed, oxygen consumption or heart rate) or it can be self-reported measurements (for example, using a validated questionnaire).

The invention further provides a composition to improve, maintain or reduce the loss of muscle function. Compositions of the invention may improve, maintain or reduce the loss of muscle function in individuals with a disease, including young and elderly individuals. Compositions of the invention may improve, maintain or reduce the loss of muscle function in healthy individuals, including athletes, non-athletic individuals, sedentary individuals and the elderly. For example, compositions of the invention may improve, maintain or reduce the loss of muscle function in frail or pre-frail individuals. For example, compositions of the invention may increase muscle strength as evidenced by the improvement of performing a physical activity, such as an exercise, for example, increased ability to lift weights or increased hand grip strength. Also, compositions of the invention may improve muscle structure, for example by increasing or maintaining muscle mass in conditions of normal muscle function, declining muscle function or impaired muscle function.

This invention further provides a composition to improve the physical performance or endurance capacity as perceived by the individual. For example, by the reduction of in perceived exertion or effort during exercise or an activity as determined using a self-reported questionnaire.

Medical Treatments:

The composition of the invention can be for use as a medicament. The compositions of the invention find use in the treatment of muscle-related pathological conditions. Accordingly, the invention provides a composition of the invention for use in the treatment of a muscle-related pathological condition. The invention also provides a method of treating a muscle-related pathological condition in a subject comprising administering to the subject an effective amount of a composition of the invention. Muscle-related pathological conditions include both conditions impacting generally healthy individuals as well as pathological conditions. Such muscle conditions found in healthy people or people affected by a disease include musculoskeletal diseases or disorders; cachexia; muscle wasting; myopathies; age-related decline in muscle function; pre-frailty; frailty; neuromuscular diseases, such as Duchenne muscular dystrophy and other dystrophies; sarcopenia, for example, acute sarcopenia; muscle atrophy and/or cachexia, for example muscle atrophy and/or cachexia associated with burns, bed rest, limb immobilization, or major thoracic, abdominal, and/or orthopedic surgery; and muscle degenerative disease.

Examples of age-related disease conditions that may be treated with compositions of the invention include sarcopenia and muscle wasting.

It has been reported in WO2014/111580 that Urolithin B (but not Urolithin A) increased the mean diameter of myotubes in vitro. The effect was not seen with Urolithin A.

Muscle Performance:

The composition of the invention is useful in enhancing muscle performance. The invention thus provides a composition of the invention for use in enhancing muscle performance. The invention also provides a method of enhancing muscle performance by administering to a subject an effective amount of a composition of the invention. Administration can be self-administration.

The enhanced muscle performance may be one or more improved muscle function, reduced decline in muscle function, improved muscle strength, improved muscle endurance and improved muscle recovery.

The composition of the invention can thus be used in a method of improving physical endurance (e.g., ability to perform a physical task such as exercise, physical labor, sports activities), inhibiting or retarding physical fatigue, enhancing working capacity and endurance, and reducing muscle fatigue.

Improved muscle function can be particularly beneficial in elderly subjects with reduced muscle function as a result of an age-related condition. For example, a subject who may benefit from improved muscle function may experience a decline in muscle function which then leads to pre-frailty and frailty. Such subjects may not necessarily experience muscle wastage in addition to their decline in muscle function. Some subjects do experience both muscle wasting and a decline in muscle function, for example subjects with sarcopenia. The composition of the invention may be used in enhancing muscle performance by administering a composition of the invention to a subject who is frail or pre-frail.

Muscle performance may be sports performance, which is to say the ability of an athlete's muscles to perform when participating in sports activities. Enhanced sports performance, strength, speed, and endurance are measured by an increase in muscular contraction strength, increase in amplitude of muscle contraction, or shortening of muscle reaction time between stimulation and contraction. Athlete refers to an individual who participates in sports at any level and who seeks to achieve an improved level of strength, speed, or endurance in their performance, such as, for example, body builders, bicyclists, long distance runners, and short distance runners. Enhanced sports performance is manifested by the ability to overcome muscle fatigue, ability to maintain activity for longer periods of time, and have a more effective workout.

EXAMPLES

The following Examples illustrate the invention.

Compounds

Urolithin A was prepared as follows:

Urolithin A (4) was prepared in two steps starting from bromide 1 and resorcinol 2. The pure compound was obtained as a pale yellow powder.

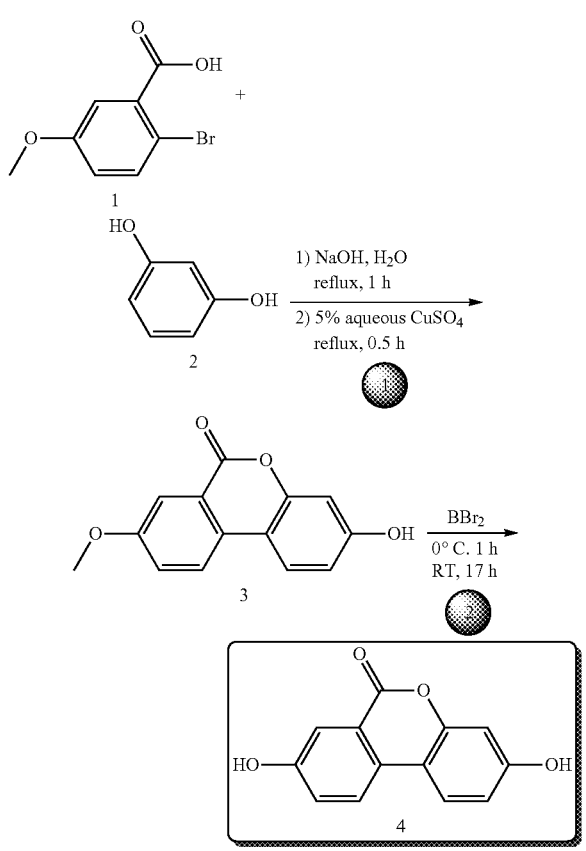

Step 1:

A mixture of 2-bromo-5-methoxybenzoic acid 1 (27.6 g; 119 mmol; 1.0 eq.), resorcinol 2 (26.3 g; 239 mmol; 2.0 eq.)

and sodium hydroxide (10.5 g; 263 mmol; 2.2 eq.) in water (120 mL) was heated under reflux for 1 hour. A 5% aqueous solution of copper sulphate (3.88 g of $CuSO_4.5H_2O$ in 50 mL water; 15.5 mmol; 0.1 eq.) was then added and the mixture was refluxed for an additional 30 minutes. The mixture was allowed to cool to room temperature and the solid was filtered on a Buchner filter. The residue was washed with cold water to give a pale red solid which was triturated in hot MeOH. The suspension was left overnight at 4° C. The resultant precipitate was filtered and washed with cold MeOH to yield the title compound 3 as a pale brown solid.

Step 2:

To a suspension of 3 (10.0 g; 41 mmol; 1.0 eq.) in dry dichloromethane (100 mL) was added dropwise at 0° C. a 1 M solution of boron tribromide in dry dichloromethane (11.93 mL of pure $BBr_3$ in 110 mL of anhydrous dichloromethane; 124 mmol; 3.0 eq.). The mixture was left at 0° C. for 1 hour and was then allowed to warm up to room temperature. The solution was stirred at that temperature for 17 hours. Then ice was added thoroughly to the mixture. The yellow precipitate was filtered and washed with cold water to give a yellow solid which was heated to reflux in acetic acid for 3 hours. The hot solution was filtered quickly and the precipitate was washed with acetic acid, then with diethyl ether to yield the title compound 4 as a yellow solid. $^1H$ and $^{13}C$ NMR were in accordance with the structure of 4.

Example 1: Experimental Trial on Muscle Function with Optimal Protein with or without Urolithin a Supplementation a) Optimal Protein Diet Containing Urolithin A To mimic age related muscle loss in humans, an experimental animal model was setup in old mice. The control diet designed to be used in the experimental study was a high protein diet that would be analogous to a clinically recommended high protein diet in elderly humans at risk of muscle loss. The diet was formulated to improve the performance of old animals that consume them. The high protein diet has a better balance of essential nutrients (amino acids, vitamins and minerals) and is supplemented with 200 gr casein per kg of diet, instead of 140 gr of casein in the regular maintenance diet (Reeves PG, J. Nutr. 1997, 127(5) 838S-841S). Casein proteins are nutritionally complete, highly digestible proteins with high amino scores that contain all amino acids in amounts sufficient to support maintenance of all body proteins. The components of the experimental high protein diet are shown in Table 5 below. Urolithin A was admixed to the high protein diet at a level of 0.57 g per kg of diet. Both the diets were isocaloric.

TABLE 5

Composition of feeds:

| Diet | High Protein Diet | | High Protein Diet + Urolithin A | |
|---|---|---|---|---|
| | gm % | Kcal % | gm % | Kcal % |
| Protein | 20 | 20 | 20 | 20 |
| Carbohydrate | 64 | 64 | 64 | 64 |
| Fat | 7 | 16 | 7 | 16 |
| Total | | 100 | | 100 |
| Kcal/gm | 4.0 | | 4.0 | |

TABLE 5-continued

Composition of feeds:

| Diet | High Protein Diet | | High Protein Diet + Urolithin A | |
|---|---|---|---|---|
| | gm % | Kcal % | gm % | Kcal % |
| Ingredient | Gm | Kcal | Gm | Kcal |
| Casein protein | 200 | 800 | 200 | 800 |
| L-Cystine | 3 | 12 | 3 | 12 |
| Corn Starch | 397.486 | 1590 | 397.486 | 1590 |
| Maltodextrin 10 | 132 | 528 | 132 | 528 |
| Sucrose | 100 | 400 | 100 | 400 |
| Cellulose, BW200 | 50 | 0 | 50 | 0 |
| Soybean Oil | 70 | 630 | 70 | 630 |
| t-butylhydroquinone | 0.014 | 0 | 0.014 | 0 |
| Mineral Mix S 100022G | 35 | 0 | 35 | 0 |
| Vitamin Mix V10037 | 10 | 40 | 10 | 40 |
| Choline Bitartarate | 2.5 | 0 | 2.5 | 0 |
| Urolithin A | 0 | 0 | 0.57 | 0 |
| FD&C Red Dye #40 | 0 | 0 | 0.05 | 0 |
| Total | 1000 | 4000 | 1000.62 | 4000 | b) Protein in Combination with Urolithin a in Diet is Better Compared with Protein Alone 22 month old C57BL/6J old mice that would be equivalent to a 65 yr to 75 yr old elderly human were treated with either the high protein diet alone or a high protein diet containing Urolithin A. Both the diets contained in addition to the casein protein, essential nutrient for optimal muscle function such as L-cysteine and vitamins and mineral mix. The level of Urolithin A in the diet results in a dose of 50 mg/kg/day delivered to mice.

Before and following 6 weeks of treatment with Urolithin A and protein combination, mice were tested for their endurance on treadmill. Endurance test was performed during the day. Mice had access to food and water before and after the exercise. The test was performed using treadmill placed in front of a motivational grid (Panlab, Barcelona, Spain). Mice were acclimatized to the treadmill for 5 minutes set on to 0.3 mA. The exercise started with 12 min running at a speed of 15 cm/second. Then speed increased by 3 cm/second every 12 minutes. The animal was removed from the treadmill when touching the back grid more than 5 times per minute during two consecutive minutes. The total distance and running time after 6 weeks of treatment was normalized over the basal values. Neither group of mice were subjected to an exercise regimen prior to the endurance test. Mice were maintained in standard animal housing throughout the course of the study.

The results of the test are shown in FIG. 1. It was strikingly observed that the mice fed with Urolithin A in addition to the high protein diet displayed an increase of 42% in running distance and 28% in running time as compared to mice receiving only a protein diet. This improvement in running endurance occurs in the absence of an exercise regimen. Statistical significance was determined using a Fischer t test. ***:$p<0.001$.

These results demonstrate the ability of Urolithin A combined with an optimal protein diet to increase muscle function in aged animals. It is anticipated that similar improvements would be observed with urolithin A in elderly humans where as standard of care today, only an optimal protein diet is recommended.

Example 2: Powder Formula Composition Targeting Healthy Aging and Age-Related Muscle Loss Containing High Protein and Urolithin A

TABLE 6

| Composition | Per 100 g (single serving) |
| --- | --- |
| Protein | 51.5 g |
| Whey | (45 g) |
| Leucine | (3.5 g) |
| Isoleucine | (1.5 g) |
| L-Arginine | (1.5 g) |
| Carbohydrates | 28 g |
| Fat | 11.5 g |
| Polyunsaturated Fatty Acids | 2.5 g |
| Fiber | 2.0 g |
| Vitamin A | 50 ug |
| Vitamin D3 | 50 ug |
| Vitamin E | 20 mg |
| Vitamin C | 100 mg |
| Vitamin B6 | 2 mg |
| Vitamin B12 | 10 ug |
| Folic Acid | 500 ug |
| Niacin | 50 mg |
| Zinc | 5 mg |
| Calcium | 100 mg |
| Selenium | 40 ug |
| Iron | 20 mg |
| Magnesium | 100 mg |
| Creatine | 1.5 g |
| Urolithin A | 1.0 g |

The composition with the nutrient profile shown in Table 6 is given to a subject to counteract age related muscle loss.

Example 3: An Enteral Nutrition Liquid Composition Targeting Immobilized Subject in Intensive Care or Hospital Settings Containing Protein and Urolithin A

TABLE 7

| Composition | Per 100 mL |
| --- | --- |
| Protein | 10.5 g |
| 100% Hydrolyzed Whey | |
| Carbohydrates | 15.4 g |
| Fat | 9.9 g |
| Polyunsaturated Fatty Acids | 3.8 g |
| Fiber | 0 g |
| Vitamin A | 170 ug |
| Vitamin D3 | 2 ug |
| Vitamin E | 3 mg |
| Vitamin C | 20 mg |
| Vitamin B6 | 0.3 mg |
| Vitamin B12 | 1 ug |
| Folic Acid | 50 ug |
| Niacin | 5 mg |
| Zinc | 1.5 mg |
| Calcium | 100 mg |
| Selenium | 10 ug |
| Iron | 2 mg |
| Magnesium | 40 mg |
| Urolithin A | 100 mg |

The drink composition with the nutrient profile shown in Table 7 is given to an immobilised subject in intensive care or a hospital setting.

Example 4: A Cereal Bar Composition Targeting an Active Athlete for Optimal Muscle Function During Endurance Training Containing Protein and Urolithin a

TABLE 8

| Composition | Per bar of 35 g |
| --- | --- |
| Energy | 600 kcal |
| Protein | 6.7 g |
| Carbohydrates | 17.2 g |
| Fat | 7.6 g |
| Polyunsaturated Fatty Acids | 3.8 g |
| Fiber | 1.6 g |
| Niacin | 25 mg |
| Zinc | 2.5 mg |
| Calcium | 180 mg |
| Sodium | 25 mg |
| Potassium | 60 mg |
| Magnesium | 80 mg |
| L-Carnitine | 200 mg |
| Urolithin A | 250 mg |

The bar composition with the nutrient profile shown in Table 8 is given to an active athlete for optimal muscle function during endurance.

Example 5: A Yogurt Composition

TABLE 9

| Nutrition value: | per 100 g | |
| --- | --- | --- |
| Fat | 0.2 g | |
| Carbohydrates | 3.7 g | |
| Protein | 9.8 g | |
| Vitamin B2 | 0.18 mg | 13% of RDA |
| Calcium | 95 mg | 12% of RDA |
| Phosphorus | 170 mg | 24% of RDA |
| Live Active Cultures | | |
| Urolithin A | 250 mg, 500 mg or 1000 mg | |

Example 6: Example 3: Effects of Particle Size on Urolithin a Bioavailability The particle size of urolithin A was reduced in a controlled manner using an MC50 Spiral Jetmill, using filtered nitrogen, with a feed rate of 240 g/hr, a Venturi pressure of 12 bar, and a mill pressure of 12 bar. Different particle size distributions of urolithin A were determined on a Malvern Particle Size analyzer (Malvern Instruments, UK). Three samples were evaluated in depth. Sample #1 of urolithin A had a particle size distribution of $D_{10}$ of 1.03 µm, a $D_{50}$ of 53.4 µm and a $D_{90}$ of 365 µm. Sample #2 of urolithin A had a particle size of $D_{10}$ of 0.272 µm, a $D_{50}$ of 2.17 µm and a $D_{90}$ of 6.84 µm. Sample #3 of urolithin A had a particle size of $D_{10}$ of 0.597 µm, a $D_{50}$ of 5.67 µm and a $D_{90}$ of 40.1 µm

TABLE 10

Particle size determinations for urolithin A before and after micronization

| Urolithin A | $D_{10}$ | $D_{50}$ | $D_{90}$ |
| --- | --- | --- | --- |
| Sample #1 | 1.03 µm | 53.4 µm | 365 µm |
| Sample #2 | 0.272 µm | 2.17 µm | 6.84 µm |
| Sample #3 | 0.597 µm | 5.67 µm | 40.1 µm |

To demonstrate the impact of particular particle size distributions on bioavailability, male Sprague-Dawley rats were fasted overnight and then administered by oral gavage with either sample #1, sample #2, or sample #3 of urolithin A suspended in 15% DMSO, 85% (0.5% methyl cellulose, 0.25% Tween 80 in Water), at a dose corresponding to 25 mg/kg/day.

TABLE 11

Design of the bioavailability study.

| Test Article | Animals N= | Dose (mg/kg) | Dosing Solution Conc. (mg/mL) | Dosing Volume (mL/kg) | Vehicle | Plasma Sampling Time Points |
|---|---|---|---|---|---|---|
| Urolithin A Sample #1 | 3 | 25 | 5 | 5 | 15% DMSO 85% (0.5% methyl cellulose/0.25% Tween 80 in Water) | Pre-dose, 0.25, 0.5, 1, 2, 4, 8, 12, 24 and 48 hours |
| Urolithin A Sample #2 | 3 | 25 | 5 | 5 | 15% DMSO 85% (0.5% methyl cellulose/0.25% Tween 80 in Water) | Pre-dose, 0.25, 0.5, 1, 2, 4, 8, 12, 24 and 48 hours |
| Urolithin A Sample #3 | 3 | 25 | 5 | 5 | 15% DMSO 85% (0.5% methyl cellulose/0.25% Tween 80 in Water) | Pre-dose, 0.25, 0.5, 1, 2, 4, 8, 12, 24 and 48 hours |

The solutions for gavage were prepared as follows: 35 mg of urolithin A powder was diluted in 7 ml of 15% DMSO, 0.5% methyl cellulose/0.25% Tween 80 in water, resulting in a 5 mg/ml fine suspension. The DMSO was obtained from BDH, methyl cellulose was obtained from Sigma, and Tween 80 was obtained from Sigma-Aldrich.

Blood was collected from the rats by jugular vein cannulation at different time points, and urolithin A was quantified in the plasma to determine its pharmacokinetic profile following oral gavage of Sample #1, Sample #2, and Sample #3. The study was repeated on three rats for each sample. FIG. 3 shows the resulting pharmacokinetic profiles of urolithin sample #1 and sample #2. The data collected is summarized below in Table 12.

TABLE 12

Results of bioavailability study for urolithin A with different particle sizes

| Parameter | Sample #1 | Sample #2 | Sample #3 |
|---|---|---|---|
| $C_{max}$ (ng/ml) | 17.1 | 37 | 17.4 |
| Relative $C_{max}$ (% of non-micronized $C_{max}$) | 100% | 216% | 102% |
| $T_{max}$ (h) | 0.25 | 0.33 | 0.50 |
| AUC | 75.1 | 96.2 | 94.8 |
| Relative bioavailability (% AUC of non-micronized urolithin A) | 100% | 128% | 126% |

Urolithin A showed an increase in bioavailability when particle size was reduced below a $D_{90}$ of 50 μm. For Sample #2 there was a relative increase in the Cmax of 116% (2.16-fold increase) and an increase in the AUC of 28%, in comparison to Sample #1. For Sample #3 there was a relative increase in the AUC of 26%.

These results demonstrate that urolithin A preparations having a particle size of $D_{90<50}$ μm consistently shows a higher bioavailability when compared to urolithin A preparations having a particle size of $D_{90}$>300 μm. Additionally, it was observed that urolithin A preparations having particle size of $D_{90}$<20 μm were especially advantageous and enabled achieving dramatically higher peak urolithin A blood levels as the Cmax achieved more than doubled.

The invention claimed is:

1. A composition comprising:
   a) a source of protein and
   b) micronized urolithin A;
   wherein the micronized urolithin A has a $D_{50}$ size in the range 0.5 to 50 μm, and a $D_{90}$ size in the range 5 to 100 μm.

2. The composition as claimed in claim 1, wherein the protein makes up 20-99% w/w of the composition.

3. The composition as claimed in claim 2 wherein the protein makes up 30-80% w/w of the composition.

4. The composition as claimed in claim 1, wherein the weight ratio between the protein component and the micronized urolithin A is in the range 2:1 to 5000:1.

5. The composition as claimed claim 1, wherein the protein is hydrolyzed.

6. The composition as claimed in claim 5, wherein the protein is derived from a source selected from milk, animal, cereal and vegetable sources.

7. The composition as claimed in claim 6 wherein the protein is selected from intact pea protein, intact pea protein isolates, intact pea protein concentrates, milk protein isolates, milk protein concentrates, casein protein isolates, casein protein concentrates, whey protein concentrates, whey protein isolates, sodium or calcium caseinates, whole cow's milk, partially or completely defatted milk, soy protein isolates and soy protein concentrates, and combinations thereof.

8. The composition as claimed in claim 1, wherein the composition is in the form of a yoghurt.

9. The composition as claimed in claim 1, wherein the composition is in the form of a solid, a semi-solid, a powder or a liquid.

10. The composition as claimed in claim 1 wherein the composition is a medicament, dietary supplement, functional food, functional beverage or medical food.

11. The composition as claimed in claim 10 wherein the composition is a medicament.

12. A method of treating a muscle-related pathological condition comprising administering to a subject in need thereof an effective amount of a composition as claimed in claim 1.

13. The method as claimed in claim 12, wherein the muscle-related pathological condition is selected from musculoskeletal diseases and disorders; muscle wasting; myopathies; neuromuscular diseases; Duchenne muscular dystrophy; sarcopenia; muscle atrophy; and cachexia.

14. A method of increasing muscle performance comprising administering to a subject an effective amount of a composition as claimed in claim 1.

15. The method as claimed in claim 14, wherein the subject suffers age-related decline in muscle function, age-related sarcopenia, age-related muscle wasting, physical fatigue, muscle fatigue, or is frail.

16. The method of claim 15, wherein the subject is frail.

17. The method of claim 15, wherein the subject suffers age-related sarcopenia.

18. The composition of claim 1 wherein the micronized urolithin A has a $D_{90}$ size in the range 8.2 to 16.0 μm, a $D_{50}$ size in the range 2.8 to 5.5 μm, and a $D_{10}$ size in the range 0.5 to 1.0 μm.

19. The method of claim 12, wherein the muscle-related pathological condition is selected from musculoskeletal diseases, musculoskeletal disorders, muscle wasting, myopathies, neuromuscular diseases, muscle atrophy, and cachexia.

20. The method of claim 12, wherein the micronized urolithin A has a $D_{90}$ size in the range 8.2 to 16.0 μm, a $D_{50}$ size in the range 2.8 to 5.5 μm, and a $D_{10}$ size in the range 0.5 to 1.0 μm.

21. The method of claim 14, wherein the micronized urolithin A has a $D_{90}$ size in the range 8.2 to 16.0 μm, a $D_{50}$ size in the range 2.8 to 5.5 μm, and a $D_{10}$ size in the range 0.5 to 1.0 μm.

* * * * *